US009454896B2

(12) United States Patent
Hocke

(10) Patent No.: US 9,454,896 B2
(45) Date of Patent: Sep. 27, 2016

(54) MEDICAL TECHNICAL APPARATUS INCLUDING A WIRELESS FOOTSWITCH DEVICE

(75) Inventor: Marc Hocke, Heerbrugg (CH)

(73) Assignee: LEICA MICROSYSTEMS (SCHWEIZ) AG, Heerbrugg (CH)

( * ) Notice: Subject to any disclaimer, the term of this patent is extended or adjusted under 35 U.S.C. 154(b) by 1640 days.

(21) Appl. No.: 13/019,380

(22) Filed: Feb. 2, 2011

(65) Prior Publication Data

US 2011/0189957 A1 Aug. 4, 2011

(30) Foreign Application Priority Data

Feb. 3, 2010 (DE) .................. 10 2010 006 845

(51) Int. Cl.
G08C 17/02 (2006.01)
A61B 17/00 (2006.01)

(52) U.S. Cl.
CPC ............. *G08C 17/02* (2013.01); *A61B 90/20* (2016.02); *A61B 2017/00221* (2013.01); *A61B 2017/00973* (2013.01)

(58) Field of Classification Search
CPC .................. G08C 17/02; A61B 90/20; A61B 2017/00973; A61B 2017/00221
USPC ........ 455/86.5, 61.29, 61.85, 41.3; 200/86.5, 200/61.29, 61.85
See application file for complete search history.

(56) References Cited

U.S. PATENT DOCUMENTS

| 7,167,911 | B2 * | 1/2007 | Heise ...................... H04L 12/12 375/219 |
| 7,428,439 | B1 | 9/2008 | Reynolds et al. |
| 7,439,463 | B2 * | 10/2008 | Brenner ............... A61C 1/0023 200/86.5 |

(Continued)

FOREIGN PATENT DOCUMENTS

| DE | 10245591 A1 | 4/2004 |
| EP | 2 033 591 A | 3/2009 |

OTHER PUBLICATIONS

IEEE Standard for Information technology—Telecommunications and information exchange between systems—Local and metropolitan area networks—Specific requirements. Part 15.4: Wireless Medium Access Control (MAC) and Physical Layer (PHY) Specifications for Low-Rate Wireless Personal Area Networks (WPANs). 802.15.4. Sep. 8, 2006, New York, NY.

*Primary Examiner* — Andrew Wendell
*Assistant Examiner* — Maryam Soltanzadeh
(74) *Attorney, Agent, or Firm* — Leydig, Voit & Mayer, Ltd.

(57) ABSTRACT

A medical technical apparatus includes an optical viewing unit including a receiver unit and a wireless footswitch device. The wireless footswitch device includes at least one switch configured to generate a control command corresponding to a performance of a function of the optical viewing unit, a transmitter unit configured to wirelessly, unidirectionally transmit data signals corresponding to the control command from the wireless footswitch device to the optical viewing unit using radio technology, a control processor, and a switching device. The switching device is configured to switch the control processor from an operating mode to a standby mode upon completion of a data transfer of the data signals from the wireless footswitch to the optical viewing unit and is also configured to switch the control processor from the standby mode to the operating mode in response to an actuation of the at least one switch for generating the control command.

14 Claims, 1 Drawing Sheet

(56) References Cited

U.S. PATENT DOCUMENTS

| | | | | |
|---|---|---|---|---|
| 8,279,374 B2* | 10/2012 | Park | ............... | G02B 21/0008 348/80 |
| 8,976,021 B2* | 3/2015 | Ozgul | ............... | A61B 5/0022 340/539.11 |
| 2003/0137723 A1* | 7/2003 | Sander | ............... | G02B 21/0012 359/380 |
| 2004/0049246 A1* | 3/2004 | Almendinger | ....... | A61B 5/0031 607/60 |
| 2007/0018844 A1 | 1/2007 | Sutardja | | |
| 2009/0058608 A1 | 3/2009 | Gottlich | | |
| 2010/0087157 A1* | 4/2010 | Takahara | ............... | 455/127.1 |
| 2010/0099956 A1* | 4/2010 | Cole | ............... | G06F 19/3418 600/300 |
| 2010/0297943 A1* | 11/2010 | Kaplan et al. | ............... | 455/41.2 |

* cited by examiner

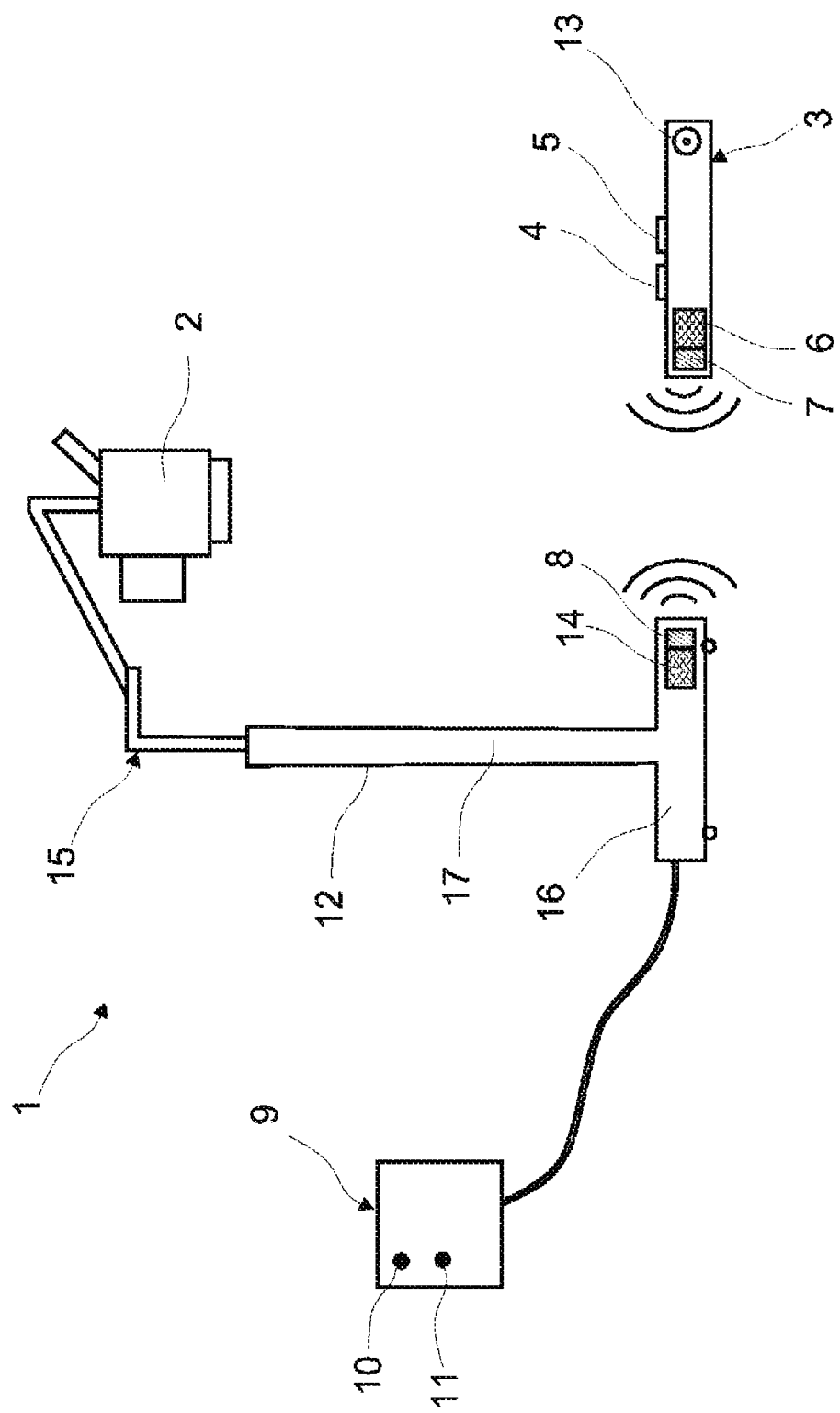

MEDICAL TECHNICAL APPARATUS INCLUDING A WIRELESS FOOTSWITCH DEVICE

CROSS REFERENCE TO RELATED APPLICATIONS

This application claims priority to German Patent Application No. DE 10 2010 006 845.4, filed Feb. 3, 2010, which is hereby incorporated by reference herein in its entirety.

FIELD

The present invention relates to a medical technical apparatus including an optical viewing unit and a wireless footswitch device including one or more switches for generating control commands to cause the optical viewing unit to perform specific functions.

BACKGROUND

Surgical microscopes are used in operating rooms during surgeries on the organism of a human or an animal, for example, to produce magnified stereoscopic images of the patient's surgical area for the human eye. The surgical microscope is used primarily in neurosurgery and eye surgery; i.e., in particular where surgeries are to be performed on very fine structures of an organism, such as on blood vessels, in the area of the spine, eye, or on the brain.

Wireless footswitch devices for controlling medical technical equipment, and especially surgical equipment, which actually constitute actuators, have important advantages over cabled footswitches. On the one hand, cables are dangerous trip hazards which are to be avoided, especially in an operating room. Moreover, conventional cables are subject to increased wear because they are heavily stressed by pieces of equipment being rolled or pushed over them. As a result, the cables must be regularly replaced by suitably trained service personnel, which requires considerable maintenance effort. On the other hand, cables having a particularly wear-resistant sheath are costly and make the device more expensive. Furthermore, the cables become dirty very easily and are difficult to clean, which is why they often do not meet the high hygienic requirements of medical applications. Moreover, cables hinder the positioning of the footswitches. Therefore, free positioning of the footswitch is possible only to a limited extent and requires extra work, such as rerouting of the cable.

Therefore, footswitches with wireless signal transmission have been described which use, for example, infrared or radio technology for transmitting signals. However, due to the limited transmission capacity and range, infrared technology is inferior to radio technology.

European Patent Publication EP-A-2 033 591, for example, describes a wireless footswitch which uses Bluetooth radio technology for signal transmission. U.S. Pat. No. 7,428,439, in turn, describes a wireless footswitch in which uses infrared radiation for information transmission. In that approach, a power source supplies electrical power to a capacitor bank, which in turn supplies electrical power to a signal generation unit.

A drawback of wireless footswitches is that they must be equipped with an autonomous power supply, which is typically provided in the form of a battery supply. The batteries used for this purpose are either replaceable, non-rechargeable batteries or rechargeable secondary batteries (storage batteries), hereinafter generally referred to as "batteries". However, in any case, the energy reserve is limited, and the batteries have to be periodically replaced or recharged.

In conventional wireless footswitches, the energy reserve of the batteries lasts from a few hours to a maximum of a few days. In order to prevent failure of the controller during use (e.g., during surgery), the operating personnel must constantly monitor the state of charge of the batteries. This situation is unsatisfactory, especially for applications in the surgical field.

The relatively short life of the batteries and the relatively high power consumption of conventional wireless footswitches are due to various reasons. For example, when using Bluetooth technology, a permanent radio link is established between the footswitch and the control unit within a particular frequency band. Bluetooth uses the frequency hopping method, in which the frequency band is divided into various discrete frequency channels, which are changed several times per second. The aforementioned characteristics of the Bluetooth technology have their advantages, but in this particular case they result in relatively high power consumption of the components. Consequently, frequent battery replacement or recharging is required.

In contrast to Bluetooth technology, ZigBee is a different, open standard for short-range wireless communication. ZigBee is a protocol stack which, in accordance with the so-called OSI model, is based on the PHY and MAC sublayers specified in the IEEE 802.15.4 standard. The protocol stack represents the conceptual architecture of network protocols in data transmission. The OSI layer model (Open Systems Interconnection Reference Model) is a specific layer model, which was developed by the International Organization for Standardization (ISO) as a basis for the design of communication protocols, such as ZigBee. The aforementioned IEEE 802.15.4 standard describes a transmission protocol and defines the two lowermost layers of the OSI model, which are referred to as physical layer (PHY) and media access control layer (MAC). The ZigBee standard defines the higher protocol layers, which provide the application interface.

Like other wireless standards (e.g., Bluetooth), ZigBee was developed for short-range wireless communication. These standards enable wireless connection of devices over short distances of, for example, from 1 to 50 meters. Advantageously, frequency transmission is implemented using the frequencies in the Industrial, Scientific and Medical (ISM) band. The ISM band was defined by the International Telecommunication Union, Radiocommunication Sector (ITU-R) and has been documented extensively in the prior art. Within the ISM band, specific frequency ranges are assigned to specific applications. For short-range wireless communication applications, for example, the frequency range between 2.402 GHz and 2.480 GHz is intended for medical-technical and industrial applications. This also applies to the ZigBee wireless standard. However, the assignment of such frequency ranges is purely administrative and not necessarily based on technical considerations. Accordingly, other frequency ranges, especially of the ISM band, could also be considered for short-range wireless communication in particular cases.

SUMMARY

In an embodiment, the present invention provides a medical technical apparatus including an optical viewing unit including a receiver unit and a wireless footswitch device. The wireless footswitch device includes at least one switch configured to generate a control command corresponding to a performance of a function of the optical viewing unit, a transmitter unit configured to wirelessly, unidirectionally transmit data signals corresponding to the control command from the wireless footswitch device to the optical viewing unit using radio technology, a control processor, and a switching device. The switching device is configured to switch the control processor from an operating mode to a standby mode upon completion of a data transfer of the data signals from the wireless footswitch to the optical viewing unit and is also configured to switch the control processor from the standby mode to the operating mode in response to an actuation of the at least one switch for generating the control command.

Embodiments of the invention also provide a footswitch device of a medical technical apparatus configured to provide data signals to an optical viewing unit, and to a method for wireless data transmission in a medical technical apparatus.

BRIEF DESCRIPTION OF THE DRAWINGS

Exemplary embodiments of the present invention are described in more detail below with reference to the drawing, in which:

FIG. 1 shows a medical technical apparatus including an optical viewing unit and a footswitch device.

DETAILED DESCRIPTION

In an embodiment, the present invention provides a medical technical apparatus including a wireless footswitch device and an optical viewing unit, as well as a method for operating such an apparatus, which are designed for low power consumption so as to increase the life of the batteries to many times that of conventional footswitches. The term "life" as used herein is understood to refer to the period of time between the first use of the battery and the time at which the battery is exhausted and needs to be replaced.

In an embodiment, the present invention includes a control processor and a transmitter unit disposed in the footswitch device and a receiver unit disposed in the optical viewing unit for wireless, unidirectional transmission of data signals from the footswitch device to the optical viewing unit, and means are provided for switching the control processor from an operating mode to a standby mode upon completion of a data transfer, and further means are provided for switching the control processor from a standby mode to the operating mode when a switch on the footswitch device is actuated to transmit a control command.

The transmitter and receiver units may include means for transmitting signals at a radio frequency defined prior to initial operation. That is, prior to the initial operation of the apparatus, the transmitter and receiver units are assigned a predefined, fixed radio frequency at which unidirectional data transmission will occur during the operating phase of the apparatus. For example, the apparatus may be set or fixed to a specific frequency already at the factory. Moreover, provision may be made for the apparatus to be set to a specific frequency after delivery and/or for the frequency to be changeable at a later time. In this manner, it is achieved that communication is only possible between a predetermined pair of a footswitch device and a viewing unit. Other wirelessly communicating devices may be excluded and, therefore, cannot interfere with the communication between the footswitch device and the viewing unit.

Moreover, provision may be made for the device to make available a defined number of frequencies from which to choose depending on whether particular frequencies are already occupied by other devices in the same room. However, during the operating phase of the device, data transmission occurs at a preset frequency. That is, the frequency is not changed during the operation of the apparatus, and, in particular, no frequency hopping occurs, as would be the case when using Bluetooth technology for example.

Further, provision is made for the radio link between the footswitch device and the viewing unit to be initialized prior to initial operation. This may already be done at the factory. That is, the radio link between the footswitch device and the viewing unit is initialized once, during which the devices identify each other, forming a permanent pair. During the operating phase, there is no need to re-introduce the devices to each other, even when the radio link is temporarily disconnected. This is because, unlike Bluetooth technology, the devices need not introduce themselves to each other when the link is re-established. Moreover, communication is only possible between the two devices that form the aforementioned pair.

In an embodiment of the present invention, the above-described pair is formed by the footswitch device and a receiver unit, said receiver unit being designed as a separate module (e.g., a plug-in module) capable of being connected to the control system of a viewing unit. When the footswitch device needs to be replaced for maintenance purposes, both the footswitch device and the associated receiver unit on the viewing unit can be replaced with a new footswitch device and receiver unit pair. To this end, after removal of the receiver unit so far used, it is only necessary to connect the receiver unit that belongs to the new footswitch device to the control system of the viewing unit.

Radio communication between the footswitch device and the optical viewing unit may be based on the ZigBee wireless standard. The footswitch device and the optical viewing unit are equipped with means suitable for implementing the ZigBee wireless technology, said means including, in particular, electronic components and data processing programs, such as operating systems and application programs.

In addition to ZigBee technology, suitable, energy-saving electronic components and an energy management system optimized for the use and management of these electronic components are also employed in the footswitch device. The optimized energy management is performed by a data processing program adapted for this task. Therefore, footswitch devices designed in accordance with embodiments of the present invention have significantly reduced power consumption. Because of this, the operational life of the batteries employed may last up to 3 years.

The footswitch device advantageously has one or more foot-operated switches for generating control commands. When such a switch is actuated to send a control command to the optical viewing unit, the control processor may generate a complete data stream including a plurality of data signals. The data signals are transmitted to the receiver in the form of radio signals. The data stream includes, for example, data signals for device identification or addressing, as well as data signals which constitute the actual control command or a sequence of sub-commands which together constitute the control command. Furthermore, provision may be made for a data stream to include a multiple, for example, triple repetition of a direct sequence of data signals in order for the control command to be transmitted to the optical viewing unit several times in immediate succession. This enhances the transmission reliability because, in contrast to transmitting the control command only once, multiple transmission increases the probability that at least one transmission is error-free. Moreover, the data may be transmitted in encrypted form for security reasons. Accordingly, means are provided for encrypting the data (footswitch device) and for decrypting the data (viewing unit).

Furthermore, the footswitch device may be provided with means adapted to determine, during the sending of a data stream, the point in time at which the last data signal of the data stream is sent or the point in time at which the control command is initiated by actuating a switch, said means further being adapted to use this information to place the control processor into a power-saving standby mode upon completion of the data transfer. The standby mode is also referred to as "suspend" or "sleep" mode, and is characterized in that the control processor is placed into a state in which large portions are turned off, which allows for savings in electrical energy as compared to the operating mode, in which all, or at least more, of the system components are active and supplied with electrical power. When reactivating the shut down system components; i.e., when changing from the standby mode to the operating mode, work can be continued immediately. Specifically, the standby mode may be characterized in that the current system configuration is loaded into a working memory while most of the other system components are turned off; i.e., (only) the working memory continues to be supplied with power. The circuits in the control processor may be designed such that as many as possible of the control processor components can be shut down in standby mode and quickly reactivated in operating mode.

Further, means are provided which are adapted to determine the point in time at which a switch on the footswitch device is actuated; i.e., the point in time at which a control command is initiated by operating a switch, so as to immediately switch the control processor from a standby mode to an operating mode.

In an embodiment, the present invention also provides a wireless footswitch device of a medical technical apparatus. The footswitch device includes a control processor and a transmitter unit for wireless, unidirectional transmission of data signals. The footswitch devices further includes means for switching the control processor from an operating mode to a standby mode once the data signals are sent, as well as means for switching the control processor from a standby mode to the operating mode to initiate a data transfer. Preferably, the footswitch device is configured to operate in accordance with the ZigBee wireless standard and equipped with the means associated therewith. In particular, the footswitch device includes corresponding electronic components and a data processing program for using the ZigBee wireless standard, as well as a data processing program for optimized energy management.

As was also mentioned hereinabove, the footswitch device can include one or more switches for generating control commands. When a switch is actuated to send a control command, a data stream including a plurality of data signals can be generated by the control processor.

In an other embodiment, the present invention provides a method for wireless control of an optical viewing unit via a footswitch device of the medical technical apparatus. The data transmission between the footswitch device and the optical viewing unit is unidirectional, the data signals being transmitted from the footswitch device to the optical viewing unit. The control processor is switched from an operating mode to a power-saving standby mode each time a data transfer is completed. Moreover, the control processor is returned from a standby mode to the operating mode each time a data transfer is to be initiated.

As described earlier, the footswitch device can include one or more switches which, when actuated (e.g., to send a control command), cause the control processor to generate a complete data stream including a plurality of data signals. Once the last data signal of this data stream has been sent, the control processor is placed into the standby mode.

Further, when a switch is actuated (e.g., to send a control command), the control processor is immediately switched from a standby mode to an operating mode, thus enabling it to generate a data stream containing the control command for transmission to the optical viewing unit.

Preferably, the radio link between the footswitch device and the optical viewing unit is maintained only during the period during which data transmission occurs. In particular, the radio link is disconnected immediately after the data transfer is completed; i.e., when or after the control processor is switched to the standby mode. The radio link is reestablished when data transfer is resumed, for example, when a new control command is initiated by actuating the footswitch device and, in particular, when the control processor is switched to the operating mode. The footswitch device is provided with corresponding means for disconnecting and reestablishing the radio link.

Thus, the radio link is preferably maintained only while the control processor is in the operating mode. This also means that the radio link is established only for a short period of time, namely when a switch is actuated to transmit a control command, and is disconnected after the transfer is completed. Thus, in general, no radio link is maintained in the period between two control commands.

The generation and transfer of a data stream containing the control command by the control processor and the transmitter unit corresponds to the period of time from the initiation of a control command by the switch to the sending of the control command in the form of radio signals (=data signals) (transmission of the last radio signal), and may take, for example, about 150 ms (milliseconds). Typically, this process does not take longer than 200 to 300 ms.

The method may provide for the control processor to be immediately switched from the standby mode to the operating mode after a control command is initiated by a switch on the footswitch device. Furthermore, the method may provide for the control processor to be returned to the standby mode after the elapse of a defined period of time after a control command is initiated by a switch on the footswitch device. The aforesaid period of time from the initiation of the control command until the control processor is switched to the standby mode is advantageously greater than the period of time needed from the initiation of the control command until the control command is sent by the transmitter to the optical viewing unit in the form of data signals. Preferably, the control processor is returned to the standby mode after less than 1 second, for example, after 200 to 1000 ms, in particular after 500 to 700 ms, and advantageously after about 600 ms after the control command is initiated by a switch. The longer the aforesaid period of time between the initiation of the control command and the activation of the standby mode, the larger the time reserve to ensure that the data stream has actually been completely transmitted and is not interrupted by the activation of the standby mode. On the other hand, too long a period of time results in significantly increased power consumption, which should also be avoided.

Moreover, the method may make provision to determine the point in time at which the last data signal of a control command has been sent by the transmitter unit. A time period is added which begins at the aforementioned particular point in time and at the end of which the control processor is switched to the standby mode. This period of time also corresponds to a safety margin which is intended ensure that the sending of the data signals and the associated processing steps are fully completed. This time period may also be less than one second, preferably less than 500 ms. For example, it may be 50 to 500 ms, in particular 100 to 400 ms.

In this manner, the power consumption of the electronic components in standby mode is minimized to a level many times less than the power consumption in operating mode. The power consumption of the electronic components may even be less than the power consumption of the employed batteries during self-discharge.

The batteries that can be used include, for example, commercially available batteries such as lithium batteries. Because of their long operational life, primary batteries may be advantageous over storage batteries. Moreover, since the footswitch device must be watertight, gas-releasing storage batteries may be disadvantageous for use in a footswitch device, unless the battery compartment is equipped with suitable gas venting valves which, on the one hand, enable gases to be vented from the storage battery and, on the other hand, ensure the watertightness of the device. A device of this kind is technically feasible, but involves additional effort and complexity.

Examples of batteries that can be used are lithium batteries (e.g., D cells), 3.6 volt, 19 Ah (ampere hours), 230 mA (milliamperes), and, in particular, lithium-thionyl chloride (Li—SOCl2) batteries.

The control processor may include a main processor and a plurality of secondary processors. Accordingly, at least the main processor, and preferably both the main processor and the secondary processors, is/are placed into a standby mode at any one time.

Moreover, the footswitch device and/or the optical viewing unit may be associated with indicator means to audibly and/or visually indicate one or more of the following operating states:
  power supply to the optical viewing unit: ON/OFF
  link between footswitch device and viewing unit established: YES/NO
  data transfer in progress: YES/NO
  battery voltage/battery charge level in the footswitch device: HIGH/MEDIUM/LOW or SUFFICIENT/LOW The visual indicator may include LEDs which, depending on the operating state, light up or not, or light up in different colors. It may be provided that when the battery charge is low, an audible signal is generated in addition to the visual indication to provide an additional indication of the low battery condition to the user. The audible signal may be sounded, for example, immediately when the critical charge level is reached and/or when the apparatus is turned off or on after a critical charge level has been reached.

Moreover, in addition, or as an alternative, to the aforementioned indicator means, provision may be made for means to enable the battery status, or an associated warning, to be projected directly into the microscope image, so that during surgery, a low battery condition is immediately indicated to the operator via the microscope image. The battery status indication may be accomplished, for example, by superimposition upon the microscope image. To this end, the indication is projected into the microscope image via a special device known in the art. Projecting the battery status, or an adequate warning of a (very) low battery status, into the microscope image may be done, for example, for safety reasons, when the battery charge has fallen to a particularly low and critical level and the battery has not yet been replaced despite an alert previously issued via the indicator means mentioned above. This allows the operator to request a battery change in time before the footswitch fails.

In order to determine the battery charge level, the footswitch device is provided with means for continuously or periodically measuring the battery voltage. As soon as the battery voltage falls below a predetermined critical level, a corresponding (visual and/or audible) indicator is activated. It may happen that the battery recovers somewhat while out of use, and that the battery voltage is then above the critical level again the next time the apparatus is used, so that no new indication of a low battery status would be issued. In order to avoid this, a threshold value is defined for the battery voltage, said threshold value being higher than the critical voltage level and selected such that once the battery voltage has reached or fallen below a critical level, it cannot exceed the threshold value anymore, even if the battery has recovered. In other words, the threshold value is selected such that it can be reached again only after battery replacement. The method is designed such that an indicator is activated when the battery voltage reaches the critical level, and that the indicator is deactivated only when the battery voltage is higher again and has reached or exceeded the aforementioned threshold value.

The footswitch device may be used, for example, to control the following operations (functions) on the optical viewing unit:
  zoom or focus adjustment;
  working distance adjustment;
  positioning, tilting or swinging of movable components of the viewing unit;
  activation of video functions;
  activation of data recording functions, etc.;
  activation of data to be projected into the microscope image;
  activation of data from foreign devices.

The activation of data (e.g., data from external foreign devices) for projection into the microscope image may include computed tomography (CT) or X-ray images or magnetic resonance imaging (MRI) images.

Energy management for the footswitch device implemented using ZigBee wireless technology has the advantage that the power consumption of the footswitch device is significantly reduced, which significantly increases the operational life of the batteries employed. With suitable selection of the batteries, it is possible to achieve an operational life of up to 3 years. This long operational life, of course, increases the reliability of the apparatus during surgical operations. In addition, the maintenance effort caused by constant battery changes or recharging is significantly reduced.

Medical technical apparatus 1 includes an optical viewing unit 15 which, in turn, includes a surgical microscope 2 mounted on a stand 12. Stand 12 includes a vertical column 17 and a base 16 by which viewing unit 15 is supported on the floor. Viewing unit 15 may be able to move across the floor on wheels provided on base 16. Stand 12 allows surgical microscope 2 to be moved over the operating table at a selected height and directly to the surgical field. Instead of a stand 12, the viewing unit may also have a suspension mechanism by which the surgical microscope is attached to the ceiling or, in some instances, to a wall.

Moreover, medical technical apparatus 1 includes a footswitch device 3, which is shown by way of example to include a first and a second switch 4, 5. The two switches 4, 5 can be actuated by the foot to send control signals to cause surgical microscope 2 to perform specific functions, such as zooming or focusing.

Footswitch device 3 further includes a control processor 6 and a transmitter unit 7, and is powered by a battery 13. Accordingly, optical viewing unit 15 includes a receiver unit 8 which is connected to control system 14 of optical viewing unit 15 and may be a separate module.

Surgical microscope 2 is an optical microscope having an optical lens system for producing magnified images of structures. Surgical microscope 2 further includes one or more binocular eyepieces for stereoscopic viewing of magnified images of the structures. Moreover, surgical microscope 2 includes means for performing zooming and focusing functions. Also provided are one or more actuators for performing the respective control functions. In addition, surgical microscope 2 may include suitable illuminating means, such as a light source.

Moreover, an indicator 9 for indicating battery status 10 and power supply status 11 via corresponding LEDs (light-emitting diodes) 10, 11 is associated with; i.e., connected to, optical viewing unit 15 and/or surgical microscope 2.

While the invention has been particularly shown and described with reference to preferred embodiments thereof, it will be understood by those skilled in the art that various changes in form and details may be made therein without departing from the spirit and scope of the invention.

LIST OF REFERENCE NUMERALS

1 medical technical apparatus
2 surgical microscope
3 footswitch device
4 first switch
5 second switch
6 control processor
7 transmitter unit
8 receiver unit
9 indicator
10 first LED
11 second LED
12 stand
13 battery
14 control system
15 optical viewing unit
16 base of the stand
17 vertical column

What is claimed is:

1. A medical technical apparatus comprising:
    an optical viewing unit of the medical technical apparatus including a receiver unit assigned to a predefined, fixed radio frequency; and
    a wireless footswitch device of the medical technical apparatus including:
        at least one switch configured to generate a control command corresponding to a performance of a function of the optical viewing unit,
        a transmitter unit configured to wirelessly, unidirectionally transmit data signals corresponding to the control command from the wireless footswitch device to the optical viewing unit at the predefined, fixed radio frequency using radio technology,
        a control processor, and
        a switching device configured to switch the control processor from an operating mode to a standby mode upon completion of a data transfer of the data signals from the wireless footswitch to the optical viewing unit and configured to switch the control processor from the standby mode to the operating mode in response to an actuation of the at least one switch for generating the control command.

2. The medical technical apparatus as recited in claim 1, wherein the optical viewing unit includes a surgical microscope.

3. The medical technical apparatus as recited in claim 1, wherein the wirelessly transmitting from the footswitch device to the viewing unit is based on the ZigBee wireless standard.

4. The medical technical apparatus as recited in claim wherein:
    the control processor is configured to generate a data stream including a plurality of data signals in response to the actuation of the at least one switch for generating the control command,
    the footswitch device is configured to switch the control processor from the standby mode to the operating mode in response to the actuation of the at least one switch for transmitting the control command, and
    the footswitch is configured to determine a point in time of the actuation of the at least one switch and to place the control processor in the standby mode after a defined time interval from the point in time of the actuation of the at least one switch has elapsed.

5. A wireless footswitch device for use in a medical technical apparatus comprising an optical viewing unit including a receiver unit assigned to a predefined, fixed radio frequency, the wireless footswitch device comprising:
    at least one switch configured to generate a control command;
    a control processor; and
    a transmitter unit for wireless, unidirectional transmission of data signals corresponding to the control command to the receiver unit of the optical viewing unit at the predefined, fixed radio frequency,
    wherein the footswitch device is configured to switch the control processor from an operating mode to a standby mode upon completion of transmission of the data signals, and is configured to switch the control processor from the standby mode to the operating mode so as to initiate a data transfer.

6. The wireless footswitch device as recited in claim 5, wherein the transmitter unit is configured to operate in accordance with the ZigBee wireless standard.

7. The wireless footswitch device as recited in claim 5, further comprising;
    a switching device configured to switch the control processor from the standby mode to the operating mode in order to generate and send a data stream including a series of data signals in response to an actuation of the at least one switch, and is configured to determine a point in time of the actuation of the at least one switch and to place the control processor in the standby mode after a defined time interval has elapsed from the point in time of the actuation of the at least one switch.

8. A method performed by a medical technical apparatus for wireless control of an optical viewing unit using a footswitch device of medical technical apparatus using radio technology, the method comprising:
    unidirectionally transmitting, by a transmitter unit, data signals corresponding to a control command generated by actuation of at least one switch of the footwitch device from the footswitch device to a receiver unit of the optical viewing unit at a predefined, fixed radio frequency so as to provide data transfers;

switching a control processor of the footswitch device from an operating mode to a power-saving standby mode after completion of each of the data transfers; and switching the control processor from the standby mode to the operating mode at initiation of each of the data transfers.

9. The method as recited in claim 8, wherein the control command corresponds to the transmitting of a data signal, and wherein actuation of the at least one switch for generating the control command results in the switching of the control processor from the standby mode to the operating mode so as to generate a complete data stream including a plurality of data signals, and wherein the switching of the control processor from the operating mode to the standby mode is carried out after sending a last data signal of the data stream.

10. The method as recited in claim 9, wherein the switching of the control processor from the standby mode to the operating mode is carried out immediately upon the actuation of the at least one switch, and the switching of the control processor from the operating mode to the standby mode is carried out after a defined time interval has elapsed from a point in time of the actuation of the at least one switch.

11. The method as recited in claim 8, further comprising assigning the fixed radio frequency to each of the transmitter and receiver units prior to an initial operation of the medical technical apparatus.

12. The method as recited in claim 8, further comprising establishing a radio link between the footswitch device and the optical viewing unit upon initiating a transmission of data signals, disconnecting the radio link after completing the transmission, and maintaining the radio link unit only during the transmission.

13. The method as recited in claim 8, further comprising establishing a radio link between the footswitch device and the optical viewing unit upon switching the control processor from the standby mode to the operating mode, disconnecting the radio link after switching the control processor from the operating mode to the standby mode, and maintaining the radio link unit only during a transmission of the data signals.

14. The method as recited in claim 8, further comprising maintaining a radio link between the footswitch device and the optical viewing unit only while the control processor is in the operating mode.

\* \* \* \* \*